(12) United States Patent
Tidwell et al.

(10) Patent No.: US 7,331,950 B2
(45) Date of Patent: Feb. 19, 2008

(54) APPARATUS FOR CONTAINING NOISE GENERATED BY A PNEUMATICALLY POWERED SURGICAL INSTRUMENT AND RELATED METHOD

(75) Inventors: Durrell G. Tidwell, Burleson, TX (US); Timothy S. Jones, Carrollton, TX (US)

(73) Assignee: Medtronic, Inc., Minneapolis, MN (US)

( * ) Notice: Subject to any disclaimer, the term of this patent is extended or adjusted under 35 U.S.C. 154(b) by 548 days.

(21) Appl. No.: 10/352,478

(22) Filed: Jan. 28, 2003

(65) Prior Publication Data

US 2004/0225293 A1 Nov. 11, 2004

Related U.S. Application Data

(60) Provisional application No. 60/387,622, filed on Jun. 11, 2002, provisional application No. 60/352,609, filed on Jan. 28, 2002.

(51) Int. Cl.
*A61B 17/00* (2006.01)

(52) U.S. Cl. .......................... 606/1; 181/175; 138/124
(58) Field of Classification Search .................. 606/1; 138/130–140, 124–126; 181/175, 212, 247, 181/252

See application file for complete search history.

(56) References Cited

U.S. PATENT DOCUMENTS

| | | | | |
|---|---|---|---|---|
| 3,185,182 A | * | 5/1965 | Medford et al. | 138/122 |
| 3,404,445 A | * | 10/1968 | Crouse | 29/890.08 |
| 4,009,382 A | | 2/1977 | Nath | |
| 5,600,752 A | * | 2/1997 | Lopatinsky | 392/488 |
| 6,481,466 B1 | * | 11/2002 | Diebolt | 138/127 |
| 6,913,112 B2 | * | 7/2005 | Bogard | 181/252 |

* cited by examiner

*Primary Examiner*—Roy D. Gibson
*Assistant Examiner*—Pete Vrettakos
(74) *Attorney, Agent, or Firm*—Haynes Boone, LLP

(57) ABSTRACT

A sound attenuating system is provided for pneumatically powered surgical instruments. In one aspect, the exhaust hose is formed of at least two dissimilar materials to impede the transmission of vibrations or audible noise. In an alternative form, the exhaust hose has proximal and distal portions of dissimilar internal diameters.

8 Claims, 3 Drawing Sheets

APPARATUS FOR CONTAINING NOISE GENERATED BY A PNEUMATICALLY POWERED SURGICAL INSTRUMENT AND RELATED METHOD

CROSS REFERENCE

The present application hereby claims the filing date priority of provisional applications U.S. Ser. Nos. 60/352,609 filed Jan. 28, 2002 and 60/387,622 filed Jun. 11, 2002, each incorporated herein by reference in their entirety. The following applications are also hereby incorporated by reference: U.S. Ser. Nos. 10/102,762 and 10/135,608.

FIELD OF THE INVENTION

The present invention relates generally to surgical instruments. More particularly, the present invention relates to powered surgical instruments for use in the dissection of bone and other tissue and a noise reducing system and method for use therewith.

BACKGROUND

Doctors and other medical professionals often use powered surgical instruments for dissecting bone and tissue. While various pneumatically powered instruments are known in the art, the high speed motors of known pneumatically powered instruments often generate an undesirable level of noise during operation. Accordingly, it remains a need in the pertinent art to provide an apparatus for more effectively containing noise generated by the motor of a pneumatically powered instrument.

SUMMARY

In general, the present invention relates to pneumatically powered instruments used in medical procedures. In one particular application, the present invention relates to an apparatus for containing noise generated by the motor of a pneumatically powered surgical instrument.

In one particular form, the present invention provides a hose assembly for a pneumatically powered instrument. The hose assembly includes a first conduit having an inner wall portion and an outer wall portion of dissimilar materials. The first conduit at least partially defines a path for the transmission of a source of exhaust gases.

In another particular form, the present invention provides a pneumatically powered instrument including a motor, a housing and a hose assembly. The motor is powered by a source of pressurized air to drive a working element. The housing defines a cavity. The hose assembly includes a first conduit and a second conduit. The first conduit includes inner and outer wall portions of dissimilar materials and at least partially defines a fluid path between the motor and the first cavity of the housing for transmitting a source of exhaust gases from the motor to the first cavity. The second conduit is concentrically arranged with the first conduit and at least partially defines a fluid path for transmitting the source of pressurized air to the motor. In a preferred aspect, the first conduit includes an area adjacent the motor having a reduced diameter and an area spaced from the motor having a diameter greater than the reduced diameter area. In a more preferred, but exemplary embodiment, an inner layer of the first conduit extends within the reduced diameter area and is absent from the larger diameter area spaced from the motor.

Advantages and features of the present invention will become apparent from the following description and appended claims, taken in conjunction with the accompanying drawings. Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description of the preferred embodiments and methods of the present invention is merely exemplary in nature and is in no way intended to limit the invention, its application, or uses. Also, it will become apparent to those skilled in the art that the subject invention is not limited to any particular surgical application but has utility for various applications in which it is desired to dissect bone or other tissue, including: arthroscopy (e.g. orthopaedic); endoscopic (e.g. gastroenterology, urology, soft tissue); neurosurgery (e.g. cranial, spine, and otology); small bone (e.g. orthopaedic, oral-maxiofacial, ortho-spine, and otology); cardio thoracic (e.g. small bone sub-segment); large bone (e.g. total joint, disease, and trauma); and dental.

Figure 1A:
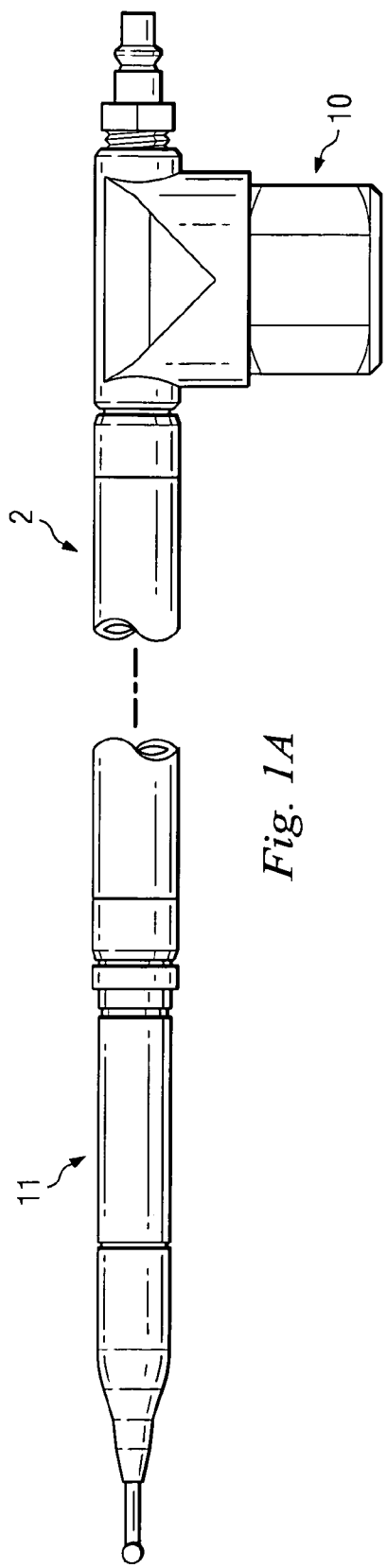
FIG. 1A is a partial side view of a hose assembly according to the teachings of a preferred embodiment of the present invention shown operatively coupled to a pneumatically powered instrument.
Figure 1B:
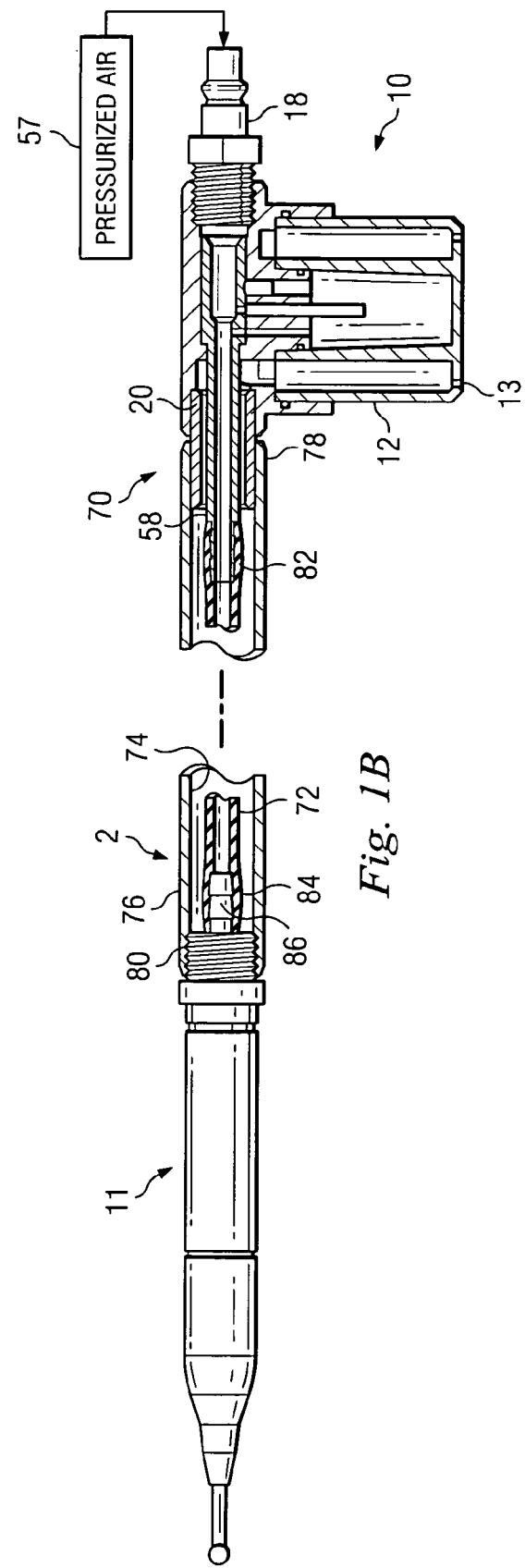
FIG. 1B is a partial cross-sectional view taken through the arrangement of FIG. 1A, the pneumatic instrument shown in simplified form.

With initial reference to FIGS. 1A and 1B, a hose assembly for a pneumatically powered instrument according to the teachings of a preferred embodiment of the present invention is illustrated and generally identified at reference character 2. The hose assembly 2 is shown operatively associated with an inline oiler cartridge assembly 10 and a pneumatically powered surgical instrument 11. A specific example of an inline oiler cartridge is disclosed in U.S. Ser. No. 10/180,470 filed Jun. 26, 2002 incorporated herein by reference in it's entirety. A suitable surgical instrument is shown in commonly assigned U.S. Pat. No. 5,505,737 which is hereby incorporated by reference as if fully set forth herein. However, it will become apparent below that the teachings of the present invention have applicability for various other pneumatically powered instruments.

With particular reference to the cross-sectional view of FIG. 1B, the hose assembly 2 is illustrated to generally include a first conduit or outer conduit 70 concentrically arranged with a second conduit or inner conduit 72. The first conduit 70 defines a portion of a fluid path for transmitting exhaust gases from a motor of the pneumatically powered instrument 11 to the ambient atmosphere through exhaust ports 13 of the housing 12. The second conduit 72 defines a portion of a fluid path for transmitting the source of pressurized air 57 to the motor of the pneumatically powered instrument 11.

In the embodiment illustrated, the first conduit 70 of the hose assembly 2 is illustrated to include an inner wall portion 74 concentrically arranged with an outer wall portion 76. A first end 78 of the first conduit 70 is shown radially surrounding a portion of the conduit 20. A second end 80 of the first conduit 70 is shown radially surrounding the motor of the pneumatically powered instrument 11.

The inner and outer wall portions 74 and 76 are preferably co-extruded of dissimilar materials. Preferably, the inner wall portion 74 is constructed of a material which is less flexible and of greater density as compared to the outer wall portion 76, such that noise generated by the motor of the pneumatically powered instrument 11 is more effectively contained. In other words, transmission of sound through the first conduit 70 is dampened. The more flexible, less dense material of the outer wall portion 76 provides characteristics desirable in environments such as an operating room. Explaining further, the outer wall portion 76 is preferably constructed of a material that can be sterilized. In one particular application, the outer wall portion 76 is preferably constructed of silicone and the inner wall portion 74 is constructed of PTFE. Those skilled in the art will however recognize that alternative materials may be incorporated within the scope of the present invention.

The second conduit 72 of the hose assembly 2 is a high pressure supply hose. A first end 82 radially surrounds the reduced diameter end 58 of the hose 18. A second end 84 radially surrounds an air inlet 86 for the motor of the pneumatically powered instrument 11. In one particular application, the second conduit 72 of the hose assembly 2 is constructed of rubber.

In operation, the source of pressurized air 57 introduces a pressurized fluid into the first conduit 18. In one particular application, the pressurized fluid is air introduced at a pressure of approximately 120 psi. In still another, the source of pressurized air 57 delivers a pressurized fluid into the first conduit 18 at a pressure of approximately 80 psi. While the term "air" is utilized throughout the description to refer to the pressurized fluid delivered to the surgical instrument to provide motive power, it is contemplated that any fluid (e.g. nitrogen) may be utilized to power the surgical instrument.

Figure 2:
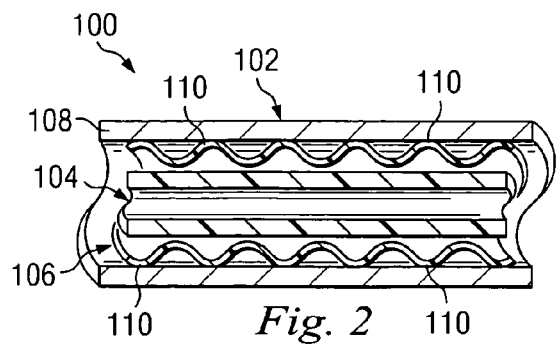
FIG. 2 is a longitudinal cross-sectional view of a hose assembly constructed in accordance with the present invention.

Turning now to the cross-sectional view of FIG. 2, a hose assembly constructed in accordance with an alternative embodiment of the present invention is illustrated and generally identified at reference number 100. As with the preferred embodiment, the hose assembly 100 is illustrated to generally include a first conduit or outer conduit 102 concentrically arranged with a second conduit or inner conduit 104. The hose assembly 100 is used in a similar manner to define a fluid path by the first conduit 102 for transmitting exhaust gases from the motor of the pneumatically powered instrument 11 to the exhaust housing and a fluid path by the second portion 104 for transmitting the source of pressurized air 57 to the motor.

The first conduit 102 of the hose assembly 100 is illustrated to include an inner wall portion 106 concentrically arranged with an outer wall portion 108. In a preferred aspect, the inner wall portion 106 is constructed from material which is less flexible and of greater density as compared to the outer wall portion 108 such that noise generated by the motor of the pneumatically powered instrument 11 is more effectively contained. The inner wall portion 106 is shown to include an inner diameter that is irregular. In the embodiment illustrated, the inner wall portion 106 comprises a convoluted tube having a plurality of radially extending ribs 110 defining a generally helical path. The convoluted tube 106 is preferably constructed of PTFE. The irregular inner diameter defined by the convoluted tube 106 functions to further introduce turbulence into the sound waves and thereby additionally dampen any noise transmitted therefrom. The tube 106 may also be constructed with concentric rings to define a corrugated structure. The tube 106 may also be formed of material identical to the material of the outer wall portion 108. Still further, the inner surface of the tube 106 may be formed to include any manner of irregular surface feature or pattern to limit the transmission of audible sound.

In the embodiment illustrated, the outer wall portion 108 is molded over the inner wall portion 106. Alternatively, the inner wall portion 106 can be inserted into the outer wall portion 108 and maintained therein by coupling or friction.

Figure 3A:
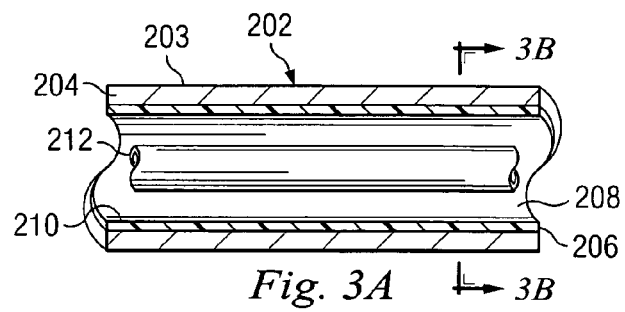
FIG. 3A is a longitudinal partial cross-sectional view of a further hose assembly constructed in accordance with another aspect of the present invention.
Figure 3B:
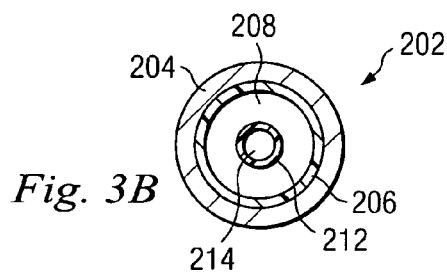
FIG. 3B is a transverse cross-sectional view taken along line 3B-3B of FIG. 3A.
Figure 6:
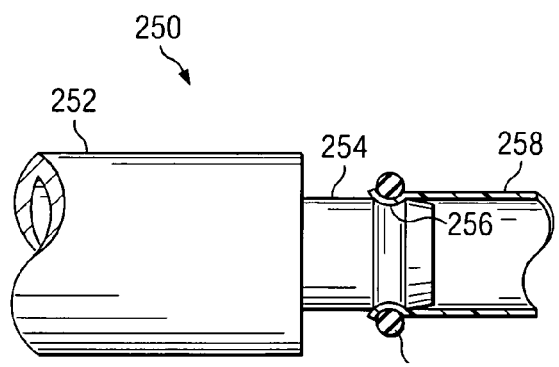
FIG. 6 is a partial cross-sectional side view of a coupling arrangement according to the present invention.

Referring now to FIGS. 3A and 3B, an alternative embodiment of a hose assembly 202 is illustrated in accordance with the present invention. Hose assembly 202 includes an outer tube or hose 203 constructed of an outer material layer 204 and an inner, dissimilar material layer 206. An exhaust passage 208 is defined between inner surface 210 of layer 206 and the outer surface of supply hose 212 having an internal passage 214 to supply pressurized fluid to a motor. In the illustrated embodiment, material layer 204 is a silicone tube and inner material layer 206 is a braided tube. Material layer 206 may be formed of, by way of example but without limitation of substitute components, braided PEEK fibers, braided Plexiglas fibers, braided copper wire with a tin coating, or fiber reinforced composite material. Further, the braiding or reinforcing components may be coated, lined or embedded with other materials to make it substantially impervious to fluids, including but without limitation, silicon, rubber, VITON® material from DuPont, PTFE, or fluorosilicon. It is contemplated that a length of the layer 206 may be inserted within layer 204 and joined to layer 204 by a variety of attachment methods without deviating from the invention. In a preferred aspect as shown in FIG. 6, tube 203 has an end 258 including a portion of each layer 204 and 206. The end 258 proximate the motor coupling 252 is coupled to the motor at fitting 254 by a wire 260 secured on the exterior adjacent annular groove 256, thereby mechanically coupling the layer 204 to the layer 206. Alternatively, the layer 206 may be bonded to the layer 204 with adhesive, heat setting, or similar bonding methods.

Figure 4:
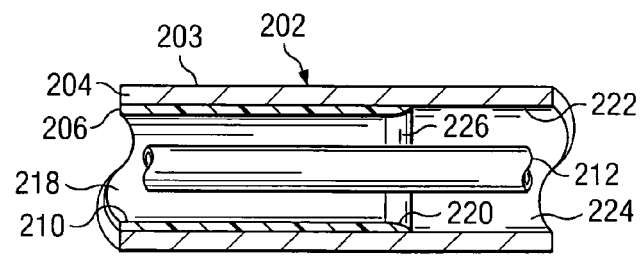
FIG. 4 is a longitudinal partial cross-sectional view of a hose assembly constructed in accordance with another aspect of the present invention.

FIG. 4 illustrates a hose assembly 202 modified in accordance with another aspect of the present invention. The components are substantially the same as those shown in FIGS. 3A and 3B and retain the same reference numbers for the purpose of illustration. In the embodiment of FIG. 4, layer 206 terminates within layer 204 forming an area 218 proximal the motor having a first diameter defined by inner surface 210 and an area 224 spaced from the motor and having a second diameter defined by inner surface 222 of layer 204. In the illustrated embodiment, layer 206 includes a transition surface 220, rather than an abrupt end, creating an area 226 having an internal diameter that gradually increases as it extends from the motor toward the exhaust ports 13 (FIG. 1B). In the exemplary embodiment of FIG. 4, the external diameter of tube 203 is substantially constant over its length between the surgical instrument and the housing 12 (FIG. 1B).

The length of layer 206 extending within layer 204 may vary depending on the design parameters of the system. One factor influencing a desired length of layer 206 is the internal diameter in area 218 and the effective back pressure experienced at the motor. For a given diameter layer 206, the back pressure at the motor may be sensed and the length adjusted to tune the system to the desired operating parameters. Alternatively, the thickness of layer 206 may be reduced, with the potential loss of sound dampening effect, to increase the internal diameter in area 218. In a preferred embodiment, but without limitation, layer 206 extends from the motor approximately 18 to 24 inches, while the complete hose assembly may have a length of between 12 to 20 feet. The relatively short length of the layer 206 provides sound damping effect immediately adjacent the motor and the user, while the remainder of the hose assembly 202 that is spaced from the user provides an increased internal diameter exhaust passage with more limited sound dampening effect. Although not illustrated, it is contemplated that passage 218 may be formed by a single material conduit and that the dissimilar material for sound attenuation may be coaxially positioned on the exterior of the assembly adjacent the motor. The length of the exteriorly positioned sound attenuating material, typically more dense or stiffer than the exhaust hose, may also be configured such that it extends only a portion of the length of the hose assembly, typically less than half the total length.

Figure 5:
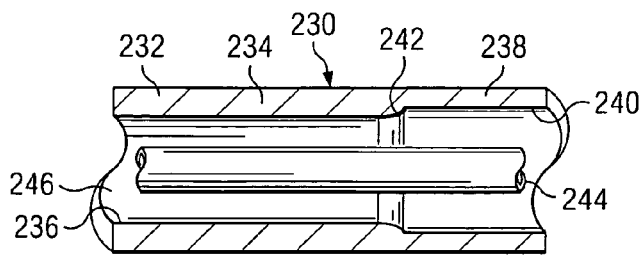
FIG. 5 is a longitudinal partial cross-sectional view of a hose assembly constructed in accordance with still another aspect of the present invention.

An alternatively constructed hose assembly 230 in accordance with another aspect of the present invention is shown in FIG. 5. Exhaust hose 232 is formed of a unitary material having a proximal portion 234 adapted for positioning adjacent to the motor 11 (FIG. 1A) and a distal portion 238 configured to be spaced from the motor and extending to the exhaust port 13 of the system. Proximal portion 234 has an increased wall thickness and an inner surface 236 defining a proximal exhaust passage with a first internal diameter greater than the external diameter of supply hose 244. As described above, the length of proximal portion 234 may be adjusted to achieve the desired balance between noise attenuation and motor performance. Distal portion 238 has a reduced wall thickness and an inner surface 240 defining a distal exhaust passage with a second internal diameter, the second internal diameter greater than the internal first diameter. The exhaust hose 232 has a transition area 242 having a wall thickness that gradually decreases from proximal portion 234 to distal portion 238 creating an exhaust passage 246 that gradually increases in internal diameter from inner surface 236 to inner surface 240. The length of the transition area 242 may extend for only a very short distance of a few millimeters to a relatively long distance of several centimeters. Alternatively, it is contemplated that there may be an abrupt transition between the proximal portion 234 and the distal portion 238 creating an internal shoulder.

In a preferred method, hose 232 is extruded from a single material, such as silicone, into the desired configuration. Further, while the illustrated embodiment shows smooth internal walls, the interior surface may be formed with irregularities to enhance sound attenuation. Alternatively, hose 232 may be molded to achieve the desired wall thickness. Still further, uniform diameter hose material may be etched or machined to remove material to form the variation in wall thickness. Although hoses having substantially circular transverse cross sections have been illustrated, it is contemplated that hoses of various cross sections may utilize the concepts of the present invention. Furthermore, while a concentric orientation of the inner and outer tubes has been illustrated and described herein, non-concentric orientation of the high pressure supply hose and the exhaust hose are herein contemplated and such configurations would also benefit from the application of the present invention.

Figure 7:
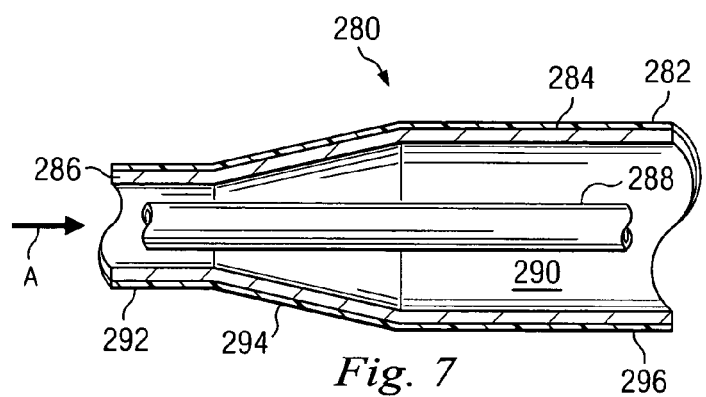
FIG. 7 is a longitudinal partial cross-sectional view of a hose assembly constructed in accordance with yet another aspect of the present invention.

A further example of the formation of an exhaust hose assembly 280 with dual internal diameters over its length is shown in the alternative embodiment of FIG. 7. Hose assembly 280 includes an exhaust line 282 and a coaxially disposed supply line 288. In the illustrated embodiment, exhaust line 282 includes an outer layer 284 and an inner layer 286 of dissimilar materials. Exhaust line 282 includes a proximal portion 292 adapted to be positioned adjacent motor 11 having a first internal diameter and a first external diameter, a distal portion 296 spaced from motor 11 and having a second, larger internal diameter and a second, larger external diameter. A transition area 294 having tapering internal and external diameters extends between the proximal portion 292 and the distal portion 296. As exhaust air flows within passage 290 in the direction of arrow A it may encounter the transition area 294 where it can undergo an expansion to a reduced pressure. As the exhaust air continues, it may undergo a further expansion as it enters distal portion 296. The gradual expansion of the exhaust air may tend to reduce audible sound in the hose assembly. Further, the use of dissimilar materials for the outer layer 284 and inner layer 286 may also contribute to attenuating sound and vibration in the system. As described above, inner layer 286 may extend only a relatively short distance from the motor. Moreover, proximal portion 292 may have a length extending from the motor (e.g. 18 to 24 inches) such that the larger diameter distal portion 296 is spaced from the motor. It will be understood that the surgical access to a patient is often limited and the application of the present invention to a surgical dissection tool may permit increased visualization and working area by decreasing the diameter of the hose assembly immediately adjacent the dissection tool.

Figure 8:
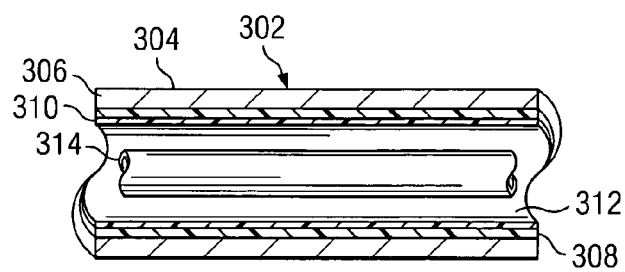
FIG. 8 is a longitudinal partial cross-sectional view of a hose assembly constructed in accordance with another aspect of the present invention.

FIG. 8 illustrates still a further embodiment of the present invention. Hose assembly 302 has an exhaust hose 304 formed of an outer layer 306, an intermediate layer 308 and an inner layer 310. The exhaust hose 304 defines a passage 312 about supply line 314. In a preferred aspect, intermediate layer 308 is a stiffer or more dense material that exhibits enhanced sound attenuation characteristics. Inner layer 310 may contribute to sound attenuation as a dissimilar material but is also selected from materials that are substantially impermeable to oil or other lubricants. Examples of such materials that may be suitable, but without limitation to further alternatives, include rubber, VITON® material, fluorosilicone, and PTFE. In some applications, it is desirable that outer layer 306 is formed of silicone which may tend to allow at least some oil to penetrate the material. Overtime, this oil may accumulate making the silicon tube slippery to the user and more prone to attract debris. As previously described, one or more of the layers may be eliminated as the hose extends from the motor. As an example, intermediate layer 308 may be eliminated approximately 18 to 24 inches from the motor, while the other two layers are continued over the length of the hose. In a preferred aspect, outer layer 306 is silicone, intermediate layer 308 is PTFE, and the inner layer 310 is VITON® material.

Alternative configurations of the present invention are contemplated herein. Some examples include the modification or substitution of material in any or all of the above described embodiments. For example, in FIG. 3 the outer layer 204 may be formed of a silicone material and the inner layer 206 may be formed of a silicone material having different durometers or hardnesses. Still further, the inner layer 206 may be formed of VITON® material thereby acting as a sound attenuation member and a barrier to lubricant penetration into the outer tube. In a preferred aspect, the at least two layers of dissimilar material forming the exhaust hose create a discontinuity in the material properties generating an acoustic impedance mismatch that tends to absorb rather than transmit vibrations or audible sound.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A surgical system, comprising:
   a pneumatically powered surgical instrument, and
   a hose assembly configured for engagement with said pneumatically powered surgical instrument, the hose assembly including,
   a first conduit having an inner wall portion concentrically and adjacently arranged with an outer wall portion, the inner and outer wall portions being of at least a first and a second dissimilar material, the first conduit at least partially defining a first fluid path for the transmission of exhaust gases from the surgical instrument, the first conduit having a first cross-sectional area for fluid flow,
   a second conduit at least partially disposed within the first conduit, the second conduit at least partially defining a second fluid path for the transmission of a pressurized fluid to the surgical instrument, the second conduit having a second cross-sectional area for fluid flow, and
   wherein the first cross-sectional area is substantially greater than the second cross-sectional area and the first dissimilar material forming the outer wall portion of the first conduit has a first flexibility and the second dissimilar material forming the inner wall portion of the first conduit has a second flexibility less than said first flexibility such that the first and second dissimilar materials forming the first conduit create a discontinuity in the material properties generating an acoustic impedance mismatch that absorbs noise generated by the pneumatically powered surgical instrument.

2. The apparatus of claim 1, wherein the second conduit is concentrically disposed within the first conduit.

3. The apparatus of claim 1, wherein the inner wall portion has an inner diameter that is irregular.

4. The apparatus of claim 3, wherein at least the inner wall portion is corrugated.

5. The apparatus of claim 1, wherein the inner wall portion is constructed of PTFE and the outer wall portion is constructed of silicone.

6. The apparatus of claim 1, wherein the first conduit has a length and the second conduit is concentrically disposed within said first conduit over a substantial portion of said length.

7. The apparatus of claim 1, wherein said first conduit has a proximal portion adapted for placement adjacent the powered surgical instrument, an opposite distal portion and a length between said proximal portion and said distal portion; wherein said outer wall portion and said inner wall portion extend substantially along the entire length.

8. The apparatus of claim 1, wherein said first conduit has a proximal portion adapted for placement adjacent the powered surgical instrument, an opposite distal portion and a length between said proximal portion and said distal portion; wherein said inner wall portion extends along only a portion of the length.

* * * * *